US011040062B2

(12) United States Patent
Friedman et al.

(10) Patent No.: US 11,040,062 B2
(45) Date of Patent: *Jun. 22, 2021

(54) SELENIUM DISULFIDE COMPOSITIONS FOR USE IN TREATING MEIBOMIAN GLAND DYSFUNCTION

(71) Applicant: Azura Ophthalmics Ltd., Tel Aviv (IL)

(72) Inventors: Doron Friedman, Carme-yosrf (IL); Yair Alster, Tel Aviv (IL); Omer Rafaeli, Udim (IL); Shimon Amselem, Rehovot (IL); Zakhar Nudelman, Netanya (IL)

(73) Assignee: AZURA OPHTHALMICS LTD., Tel Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/093,615

(22) PCT Filed: Apr. 13, 2017

(86) PCT No.: PCT/IB2017/000542
§ 371 (c)(1),
(2) Date: Oct. 12, 2018

(87) PCT Pub. No.: WO2017/178892
PCT Pub. Date: Oct. 19, 2017

(65) Prior Publication Data
US 2020/0281966 A1 Sep. 10, 2020

Related U.S. Application Data

(60) Provisional application No. 62/322,627, filed on Apr. 14, 2016.

(51) Int. Cl.
| A61K 33/04 | (2006.01) |
| A61K 9/00 | (2006.01) |
| A61K 9/06 | (2006.01) |
| A61K 9/16 | (2006.01) |
| A61K 47/06 | (2006.01) |
| A61K 47/44 | (2017.01) |

(52) U.S. Cl.
CPC ............ *A61K 33/04* (2013.01); *A61K 9/0048* (2013.01); *A61K 9/06* (2013.01); *A61K 9/16* (2013.01); *A61K 47/06* (2013.01); *A61K 47/44* (2013.01)

(58) Field of Classification Search
CPC . A61K 33/04; A61K 9/00; A61K 9/06; A61K 9/16; A61K 47/06; A61K 47/44
See application file for complete search history.

(56) References Cited

U.S. PATENT DOCUMENTS

| 3,236,730 | A | 2/1966 | Galin |
| 5,645,827 | A | 7/1997 | Marlin et al. |
| 6,348,508 | B1 | 2/2002 | Denick, Jr. et al. |
| 7,288,259 | B2 | 10/2007 | Sanders et al. |
| 8,449,928 | B2 | 5/2013 | Gilbard et al. |
| 8,455,016 | B2 | 6/2013 | Maskin |
| 9,463,201 | B2 * | 10/2016 | Alster ............... A61K 31/60 |
| 10,034,887 | B2 | 7/2018 | Alster et al. |
| 10,588,915 | B2 | 3/2020 | Alster et al. |
| 2004/0171561 | A1 | 9/2004 | Popp |
| 2004/0192647 | A1 | 9/2004 | Babizhayev |
| 2005/0124690 | A1 | 6/2005 | Yoon et al. |
| 2005/0197614 | A1 | 9/2005 | Pritchard et al. |
| 2006/0188471 | A1 | 8/2006 | Podolsky et al. |
| 2007/0082017 | A1 | 4/2007 | Tseng et al. |
| 2007/0166402 | A1 | 7/2007 | Friedlaender et al. |
| 2007/0269537 | A1 | 11/2007 | Gupta |
| 2008/0103376 | A1 | 5/2008 | Felder |
| 2008/0242729 | A1 * | 10/2008 | Bollag ............... A61P 21/04 514/569 |
| 2009/0214676 | A1 | 8/2009 | Gao et al. |
| 2010/0034870 | A1 | 2/2010 | Sim et al. |
| 2010/0204317 | A1 | 8/2010 | Hunt et al. |
| 2010/0256552 | A1 | 10/2010 | Korb et al. |
| 2010/0285155 | A1 | 11/2010 | Gilbard et al. |
| 2011/0022010 | A1 | 1/2011 | Grenon et al. |
| 2011/0059925 | A1 | 3/2011 | Donnenfeld |
| 2011/0124725 | A1 | 5/2011 | Maskin |
| 2011/0130729 | A1 | 6/2011 | Korb et al. |
| 2011/0137214 | A1 | 6/2011 | Korb et al. |
| 2011/0294897 | A1 | 12/2011 | Aberg et al. |
| 2012/0016275 | A1 | 1/2012 | Korb et al. |

(Continued)

FOREIGN PATENT DOCUMENTS

| CN | 101612161 A | 12/2009 |
| CN | 105456287 A | 4/2016 |

(Continued)

OTHER PUBLICATIONS

PCT/IB2017/000542 International Preliminary Report on Patentability dated Oct. 25, 2018.
PCT/IB2017/00542 International Search Report and Written Opinion dated Sep. 21, 2017.
U.S. Appl. No. 16/919,749 Office Action dated Oct. 5, 2020.
Maskin. Intraductal meibomian gland probing relieves symptoms of obstructive meibomian gland dysfunction. Cornea 29(10):1145-1152 (2010).

(Continued)

Primary Examiner — Shirley V Gembeh

(74) Attorney, Agent, or Firm — Wilson Sonsini Goodrich & Rosati

(57) ABSTRACT

Described herein are compositions and methods for the treatment of meibomian gland dysfunction. Said methods are performed by administering said composition comprising a selenium disulfide and an anhydrous semi-solid base. The stable anhydrous composition are substantially free of selenium disulfide agglomerates.

22 Claims, 2 Drawing Sheets

(56) References Cited

U.S. PATENT DOCUMENTS

| | | |
|---|---|---|
| 2012/0028929 A1 | 2/2012 | Power et al. |
| 2012/0093876 A1 | 4/2012 | Ousler, III et al. |
| 2012/0128763 A1 | 5/2012 | Maskin |
| 2012/0190661 A1 | 7/2012 | Trogden et al. |
| 2012/0226156 A1 | 9/2012 | Grenon et al. |
| 2012/0264681 A1 | 10/2012 | Braiman-Wiksman et al. |
| 2012/0288575 A1 | 11/2012 | Gilbard et al. |
| 2013/0053733 A1 | 2/2013 | Korb et al. |
| 2013/0131171 A1 | 5/2013 | Maskin |
| 2013/0184242 A1 | 7/2013 | Eini et al. |
| 2013/0224272 A1 | 8/2013 | Gao et al. |
| 2013/0274214 A1 | 10/2013 | Brubaker |
| 2013/0280340 A1 | 10/2013 | Dobbie |
| 2013/0281390 A1 | 10/2013 | Brubaker |
| 2013/0331768 A1 | 12/2013 | Nichamin |
| 2013/0344128 A1 | 12/2013 | Gao et al. |
| 2013/0345185 A1 | 12/2013 | Mitra et al. |
| 2014/0005171 A1 | 1/2014 | Aukunuru et al. |
| 2014/0058340 A1 | 2/2014 | Guillon et al. |
| 2014/0142055 A1 | 5/2014 | Hosseini et al. |
| 2014/0142668 A1 | 5/2014 | Guillon et al. |
| 2014/0154333 A1 | 6/2014 | Moloney |
| 2014/0206708 A1 | 7/2014 | Ren et al. |
| 2019/0388440 A1 | 12/2019 | Alster et al. |
| 2020/0330488 A1 | 10/2020 | Alster et al. |

FOREIGN PATENT DOCUMENTS

| | | |
|---|---|---|
| EP | 0930072 A1 | 7/1999 |
| EP | 1621191 A1 | 2/2006 |
| EP | 2633852 A1 | 9/2013 |
| WO | WO-9611686 A1 | 4/1996 |
| WO | WO-9724116 A2 | 7/1997 |
| WO | WO-03035076 A1 | 5/2003 |
| WO | WO-03050190 A2 | 6/2003 |
| WO | WO-2007070463 A2 | 6/2007 |
| WO | WO-2007133703 A2 | 11/2007 |
| WO | WO-2008027069 A1 | 3/2008 |
| WO | WO-2010006117 A2 | 1/2010 |
| WO | WO-2012092320 A2 | 7/2012 |
| WO | WO-2012161112 A1 | 11/2012 |
| WO | WO-2013003731 A2 | 1/2013 |
| WO | WO-2015022546 A1 | 2/2015 |
| WO | WO-2016063130 A1 | 4/2016 |
| WO | WO-2017178892 A2 | 10/2017 |
| WO | WO-2017182885 A2 | 10/2017 |

OTHER PUBLICATIONS

Nelson et al. The International Workshop on Meibomian Gland-Dysfunction: Report of the Definition and Classification Subcommittee. Invest Ophthalmol Vis Sci. 52(4):1930-1937 (2011).

Nichols. The International Workshop on Meibomian Gland Dysfunction: Introduction. Invest Ophthalmol Vis Sci 52(4):1917-1921 (2011).

PCT/IB2015/02164 International Search Report and Written Opinion dated Mar. 29, 2016.

U.S. Appl. No. 14/732,622 Office Action dated Nov. 19, 2015.
U.S. Appl. No. 15/269,833 Office Action dated Aug. 7, 2017.
U.S. Appl. No. 15/269,833 Office Action dated Jan. 11, 2017.
U.S. Appl. No. 16/019,253 Office Action dated May 16, 2019.
U.S. Appl. No. 16/562,374 Office Action dated Oct. 30, 2019.

Wong et al. Selenium (Selsun) in the Treatment of Marginal Blepharitis. AMA Arch Ophthalmol 55(2):246-253 (1956).

* cited by examiner

SELENIUM DISULFIDE COMPOSITIONS FOR USE IN TREATING MEIBOMIAN GLAND DYSFUNCTION

CROSS REFERENCE

This application is the U.S. National Stage Patent Application of International Patent Application No. PCT/IB2017/000542, filed Apr. 13, 2017, which claims the benefit of U.S. Provisional Application No. 62/322,627, filed Apr. 14, 2016, all of which are incorporated by reference herein in their entirety.

BACKGROUND OF THE INVENTION

Meibomian gland dysfunction (MGD) is a leading contributor to dry eye syndrome and is often characterized by keratin-based obstruction of the gland, reduction in meibum quantity and quality, and increased viscosity of lipids produced by meibomian glands. Described herein are anhydrous selenium disulfide formulations which are chemically and physically stable, substantially free of aggregates, and substantially free of surfactants and dispersing agents. Such formulations show minimal diffusion onto the ocular surface. Also provided are methods for use of the formulations in the treatment of meibomian gland dysfunction.

SUMMARY OF THE INVENTION

One embodiment provides a composition for treating meibomian gland dysfunction comprising selenium disulfide and an anhydrous semi-solid ophthalmic base, wherein the composition is substantially free of selenium disulfide agglomerates, wherein the composition is substantially free of surfactants and dispersing agents, and wherein the composition is suitable for topical administration on the eyelid margin.

Another embodiment provides the composition wherein the selenium disulfide is dispersed in the anhydrous semi-solid ophthalmic base.

Another embodiment provides the composition wherein the anhydrous semi-solid ophthalmic base is an oleaginous base. Another embodiment provides the composition wherein the oleaginous base is selected from a group consisting of petroleum, white petroleum, and vegetable oils. Another embodiment provides the composition wherein the oleaginous base is selected from a group consisting of petroleum, white petroleum, mineral oil, vegetable oils and combinations thereof.

Another embodiment provides the composition wherein the anhydrous semi-solid ophthalmic base is prepared for use as a lip balm-like or stick formulation.

Another embodiment provides the composition wherein the composition has a melting point between about 34° C. and about 50° C.

Another embodiment provides the composition further comprising degradants of selenium disulfide, and wherein the amount of the degradants does not increase during a storage period, under accelerated stability conditions, at a temperature of about 40° C. Another embodiment provides the composition further comprising small amounts of degradants of selenium disulfide, and wherein the amount of the degradants does not increase above 1% of the total weight of the composition.

Another embodiment provides the composition wherein the composition exhibits no substantial color change, upon exposure to a temperature of about 60° C. for a period of time, and wherein the color change is determined by a colorimetric assay.

Another embodiment provides the composition wherein the composition further comprises squalene.

Another embodiment provides the composition wherein the composition further comprises hydrogenated oil.

Another embodiment provides the composition wherein the composition being substantially free of selenium disulfide agglomerates is an ointment/semi-solid defined as having an average selenium disulfide particle diameter of less than about 50 μm.

Another embodiment provides the composition wherein a composition being substantially free of selenium disulfide agglomerates is an ointment/semi-solid defined as having an average selenium disulfide particle diameter of about 5 μm and about 10 μm.

One embodiment provides a method for treating meibomian gland dysfunction in a patient in need thereof, comprising topically administering to the eyelid margin of the patient a composition comprising selenium disulfide and an anhydrous semi-solid ophthalmic base, wherein the composition is substantially free of selenium disulfide agglomerates, and wherein the composition is substantially free of surfactants and dispersing agents.

Another embodiment provides the method wherein the selenium disulfide is dispersed in the anhydrous semi-solid ophthalmic base. Another embodiment provides the method wherein the anhydrous semi-solid ophthalmic base is an oleaginous base. Another embodiment provides the method wherein the oleaginous base is selected from the group consisting of petroleum, white petroleum, and vegetable shortenings. Another embodiment provides the composition wherein the oleaginous base is selected from a group consisting of petroleum, white petroleum, mineral oil, vegetable oils and combinations thereof.

Another embodiment provides the method wherein the composition for topical administration has a melting point between about 34° C. and about 50° C.

Another embodiment provides the method wherein the composition for topical administration is stable under accelerated stability conditions, at a temperature of about 40° C.

Another embodiment provides the method wherein the composition for topical administration further comprises degradants of selenium disulfide, and wherein the amount of the degradants does not increase during a storage period, under accelerated stability conditions, at a temperature of about 40° C. Another embodiment provides the composition further comprising small amounts of degradants of selenium disulfide, and wherein the amount of the degradants does not increase above 1% of the total weight of the composition.

Another embodiment provides the method wherein the composition for topical administration exhibits no substantial color change, upon exposure to a temperature of about 60° C. for a period of time, and wherein the color change is determined by a colorimetric assay.

Another embodiment provides the method wherein the composition for topical administration further comprises squalene.

Another embodiment provides the method wherein the composition for topical administration is an ointment.

Another embodiment provides the method wherein the meibomian gland dysfunction is characterized by obstruction of meibomian gland.

Another embodiment provides the method wherein topical administration of the composition comprising selenium disulfide and an anhydrous ophthalmic base occurs until the meibomian gland obstruction is substantially removed.

Another embodiment provides the method wherein topical administration of the composition comprising selenium disulfide and an anhydrous ophthalmic base occurs periodically after removal of the meibomian gland obstruction, to prevent formation of a new meibomian gland obstruction.

Another embodiment provides the method wherein the composition being substantially free of selenium disulfide agglomerates is defined as a composition having an average selenium disulfide particle diameter of less than about 50 µm.

Another embodiment provides the method wherein the composition being substantially free of selenium disulfide agglomerates is defined as a composition having an average selenium disulfide particle diameter of between about 5 µm and about 10 µm.

One embodiment provides a method for treating meibomian gland dysfunction in a patient in need thereof, comprising topically administering to the eyelid margin of the patient a composition consisting of selenium disulfide and an anhydrous semi-solid ophthalmic base, wherein the composition is substantially free of selenium disulfide agglomerates, wherein the composition is substantially free of surfactants and dispersing agents, wherein the meibomian gland dysfunction is characterized by obstruction of meibomian gland and increased viscosity of meibum, and wherein the method results in substantial removal of the meibomian gland obstruction.

BRIEF DESCRIPTION OF THE FIGURES

FIG. 1 illustrates microscopic images of various selenium disulfide formulations in aqueous media.

FIG. 2 illustrates microscopic images of anhydrous selenium disulfide formulations.

DETAILED DESCRIPTION OF THE INVENTION

Described herein are compositions useful for treating meibomian gland dysfunction. Said compositions comprise anhydrous selenium disulfide ($SeS_2$) wherein the $SeS_2$ is dispersed in an anhydrous vehicle in a non-aggregated manner and the dispersion of $SeS_2$ is stable physically and chemically without use of surfactants, suspending agents or dispersing agents.

Figure 1A:
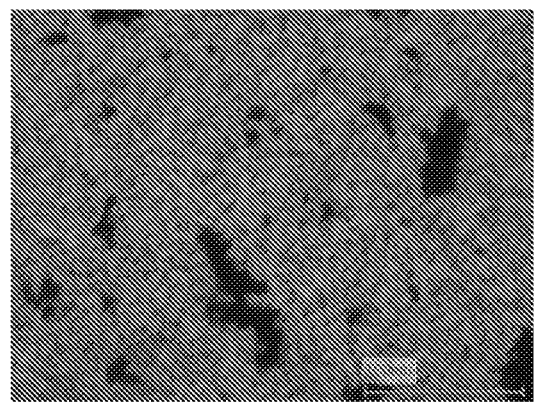
FIGS. 1A, 1B, and 1C correspond to microscopic images of a Sebosel™ formulation, at 200× magnification, a dispersion of selenium disulfide in water at room temperature, at 100× magnification, and a 2.5% selenium disulfide formulation in Carbopol™ gel magnification at 100× magnification, respectively.
Figure 1B:
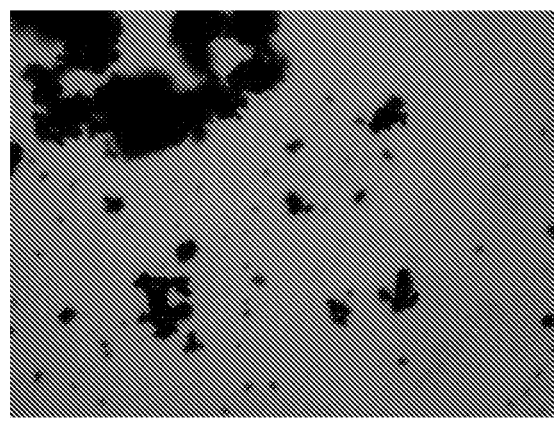
Figure 1C:
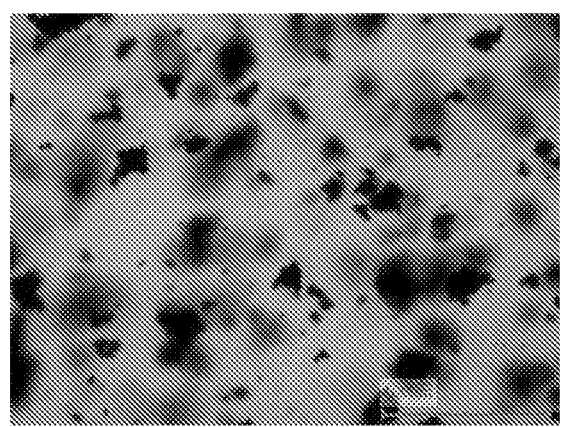

Contacting $SeS_2$ with aqueous medium causes immediate and spontaneous aggregation, such that $SeS_2$ particles with an average size of 5 to 10 microns will form large aggregates of 50 to 500 microns average size. $SeS_2$ in marketed products (e.g., Sebosel™) is present in such aggregates (FIG. 1). Surfactants and various suspending agents are required to stabilize $SeS_2$ suspension in liquid and semi-solid dosage forms in order to enable its topical application.

Unexpectedly, we have been able to achieve a stable suspension of $SeS_2$ by using an anhydrous semi-solid dosage forms without the use of surfactants or suspending agents. Additionally, the dispersion is substantially free of large aggregates and the suspended $SeS_2$ particles are evenly and homogeneously dispersed and distributed and therefore a high content uniformity is obtained.

Moreover, $SeS_2$ tends to degrade over time upon prolonged storage, and the degradation products have undesirable properties, such as increased toxicity. The developed suspension of $SeS_2$ has extremely improved chemical stability compared to currently marketed products. This improved stability is particularly important for ophthalmic applications since the ocular surface is more sensitive than the skin to $SeS_2$ degradation products. It has been observed that $SeS_2$ aqueous suspensions change color from orange to brown/gray colors at accelerated temperature conditions. Such discoloration indicates chemical degradation of the $SeS_2$ cyclic ring structure. The anhydrous and surfactant free formulation of $SeS_2$ disclosed herein does not degrade at the rate of the currently available $SeS_2$ compositions and is therefore much more suitable for ophthalmic use.

Previously Tseng described (US 2007/0082017) an ointment comprising a lipid composition to treat dry eye by applying the ointment to the inferior lid margin and by allowing diffusion of the lipid composition to the eye to integrate into tear film. However, in order to achieve sustained release of the ointment and to prevent a blurring of vision by the ointment by good dispersion tear fluid, Tseng is using a surfactant. The present invention relates to a composition applying to the eyelid having no surfactant. In the absence of surfactant, the present formulation tends to mix much less with tear fluid.

Stable Anhydrous Selenium Disulfide Formulations

Described herein in some embodiments are stable anhydrous formulations of selenium disulfide which are chemically stable, substantially free of aggregates and agglomerates. In some embodiments, the stable anhydrous selenium sulfide formulations described herein are substantially free of surfactants. In some embodiments, the stable anhydrous selenium sulfide formulations described herein are substantially free of dispersing agents. In some embodiments, the stable anhydrous selenium disulfide formulations described herein, contain about 0.05% to about 5% selenium disulfide. In some embodiments, the stable anhydrous selenium disulfide formulations described herein, contain about 2.5% selenium disulfide. In some embodiments, the stable anhydrous selenium disulfide formulations described herein, contain about 0.01% to about 10% selenium disulfide. In some embodiments, the stable anhydrous selenium disulfide formulations described herein, contain about 0.01% selenium disulfide. In some embodiments, the stable anhydrous selenium disulfide formulations described herein, contain about 0.05% selenium disulfide. In some embodiments, the stable anhydrous selenium disulfide formulations described herein, contain about 0.1% selenium disulfide. In some embodiments, the stable anhydrous selenium disulfide formulations described herein, contain about 0.5% selenium disulfide. In some embodiments, the stable anhydrous selenium disulfide formulations described herein, contain about 1.0% selenium disulfide. In some embodiments, the stable anhydrous selenium disulfide formulations described herein, contain about 1.5% selenium disulfide. In some embodiments, the stable anhydrous selenium disulfide formulations described herein, contain about 2.0% selenium disulfide. In some embodiments, the stable anhydrous selenium disulfide formulations described herein, contain about 2.5% selenium disulfide. In some embodiments, the stable anhydrous selenium disulfide formulations described herein, contain about 3.0% selenium disulfide. In some embodiments, the stable anhydrous selenium disulfide formulations described herein, contain about 3.5% selenium disulfide. In some embodiments, the stable anhydrous selenium disulfide formulations described herein, contain about 4.0% selenium disulfide. In some embodiments, the stable anhydrous selenium disulfide formulations described herein, contain about 4.5% selenium disulfide. In some embodiments, the stable anhydrous selenium disulfide formulations described herein, contain about 5.0% selenium disulfide. In some embodiments, the stable anhydrous selenium disulfide formulations described herein, contain about 5.5% selenium disulfide. In some embodiments, the stable anhydrous selenium disulfide formulations described herein, contain about 6.0% selenium disulfide. In some embodiments, the stable anhydrous selenium disulfide formulations described herein, contain about 6.5% selenium disulfide. In some embodiments, the stable anhydrous selenium disulfide formulations described herein, contain about 7.0% selenium disulfide. In some embodiments, the stable anhydrous selenium disulfide formulations described herein, contain about 7.5% selenium disulfide. In some embodiments, the stable anhydrous selenium disulfide formulations described herein, contain about 8.0% selenium disulfide. In some embodiments, the stable anhydrous selenium disulfide formulations described herein, contain about 8.5% selenium disulfide. In some embodiments, the stable anhydrous selenium disulfide formulations described herein, contain about 9.0% selenium disulfide. In some embodiments, the stable anhydrous selenium disulfide formulations described herein, contain about 9.5% selenium disulfide. In some embodiments, the stable anhydrous selenium disulfide formulations described herein, contain about 10.0% selenium disulfide.

In some embodiments, the anhydrous semi-solid base is an oleaginous base. Exemplary oleaginous bases, for the stable anhydrous selenium disulfide formulations described herein include petroleum base, mineral oil, a mixture of mineral oil and white petroleum, vegetable oil, or petroleum jelly (Vaseline®). In some embodiments, the vegetable oil is chosen from coconut oil, fractionated coconut oil, jojoba oil, olive oil, sunflower oil, almond oil, cod liver oil, castor oil or virgin wax In some embodiments, the stable anhydrous selenium disulfide formulations further comprise an oil. In some embodiments, the oil is chosen from a triglycerides, diglyceride, monoglycerides, acetylated lanolin alcohol, alkyl benzoate, an alkyl octanoate, almond oil, an unsaturated or polyunsaturated oil, apricot stone oil, arachidyl behenate, arachidyl propionate, avocado oil, barley oil, basil oil, beeswax, benzyl laurate, benzyl myristate, benzyl palmitate, bis (octyldodecyl stearoyl) dimer dilinoleate, borage seed oil, butyl myristate, butyl stearate, C12-C15 alkyl benzoate, C12-C15 alkyl octanoate, calendula oil, camphor oil, canelle nut tree oil, canola oil, capric/caprylic triglycerides, caprylic/capric triglyceride castor oil, caprylyl methicone, cardamom oil, carrot oil, castor oil, cetearyl ethylhexanoate, cetearyl isononanoate, cetearyl octanoate, cetyl acetate, cetyl dimethicone, cetyl ethylhexanoate, cetyl lactate, cetyl myristate, cetyl octanoate, cetyl palmitate, cetyl ricinoleate, citronella oil, clary sage oil, clove oil, cocoglycerides, coconut oil, cod-liver oil, corn oil, cotton oil, cottonseed oil, cyclohexasiloxane, cyclomethicone, cyclomethicone 5-NF (cyclopentasiloxane), cyclotetrasiloxane, cypress oil, decyl oleate, diethyleneglycol, diethylhexanoate, diethyleneglycol diisononanoate, diethyleneglycol dioctanoate, diethylhexanoate, diethylhexyl adipate, diethylhexyl malate, diethylhexyl succinate, diisopropyl adipate, diisopropyl dimerate, diisopropyl sebacate, diisostearyl dimer dilinoleate, diisostearyl fumarate, dimethicone, dimethyl polysiloxane, dioctyl malate, dioctyl sebacate, disopropyl adipate, dodecyl oleate, cyclotetrasiloxane (Dow Corning 244 Fluid), cyclohexasiloxane/cyclopentasiloxane (Dow corning 246 Fluid (d6+ d5)), epoxy-modified silicone oil, ester derivatives of lanolic acid, ethylhexyl cocoate, ethylhexyl ethylhexanoate, ethylhexyl hydroxystarate, ethylhexyl isononanoate, ethylhexyl palmitate, ethylhexyl palmytate, ethylhexyl pelargonate, ethylhexyl stearate, evening primrose oil, fatty acid-modified silicone oil, flaxseed oil, fluoro group-modified silicone oil, frankincense oil, gelled mineral oil, ginger oil, glycereth triacetate, glycerol triheptanoate, glyceryl oleate, glyceryl trioctanoate, glyceryl triundecanoate, grape seed oil, grapefruit oil, groundnut oil, hazelnut oil, heavy mineral oil, hemp seed oil, herring oil, hexadecyl stearate, hexyl laurate, hydrocarbon oils, hydrogenated castor oil, hyssop oil, isoamyl laurate, isocetearyl octanoate, isocetyl isocetyl behenate, isocetyl lanolate, isocetyl palmitate, isocetyl salicylate, isocetyl stearate, isocetyl stearoyl stearate, isodecyl ethylhexanoate, isodecyl isononanoate, isodecyl oleate, isododecane, isohexadecane isododecane, isohexadecanol, isohexyl decanoate, isononyl isononanoate, isononyl octanoate, isoparaffin, isopropyl isostearate, isopropyl lanolate, isopropyl laurate, isopropyl myristate, isopropyl palmitate, isopropyl stearate, isosteary citrate, isosteary salicylate, isosteary tartarate, isostearyl behenate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isotridecyl isononanoate, jasmine oil, lauryl lactate, lavender oil, lemon oil, light mineral oil, liquid paraffin, liquid triglycerides, lucerne oil, maize germ oil, maleated soybean oil, mandarin oil, manuka oil, marjoram oil, marrow oil, MCT oil, methylphenylpolysiloxane, millet oil, mineral oil, myristyl lactate, myristyl myristate, myristyl neopentanoate, myristyl propionate, myrrh oil, neopentylglycol dicaprate, neopentylglycol dicaprylate/dicaprate, neroli oil, nutmeg oil, octyl palmitate, octyl stearate, octyldodecanol, octyldodecyl behenate, octyldodecyl hydroxystearate, octyldodecyl myristate, octyldodecyl stearoyl stearate, oils from animal origin, oils of plant origin, oleyl erucate, oleyl lactate, oleyl oleate, olive oil, dimethiconol, palm oil, passionflower oil, peanut oil, rapeseed oil, rosehip oil, rye oil, safflower oil, sage oil, salmon oil, sesame oil, shea butter, silicone oils, soya oil, soybean oil, stearyl caprate, stearyl dimethicone, stearyl heptanoate, stearyl propionate, sunflower oil, sweet almond oil, synthetic isoalkane, sysymbrium oil, syzigium aromaticum oil, tangerine oil, tea tree oil, therapeutic oils, tocopheryl acetate, tocopheryl linoleate, tridecyl ethylhexanoate, tridecyl isononanoate, triisocetyl citrate, unsaturated or polyunsaturated oils, vanilla oil, verbena oil, walnut oil, wheat germ glycerides, wheat germ oil, white petrolatum and mixtures thereof.

In some embodiments, the stable anhydrous selenium disulfide formulations described herein further comprise an oil chosen from caprylic acid triglyceride, isopropyl palmitate and isopropylpalmitate. In some embodiments, the stable anhydrous selenium disulfide formulations described herein further comprise caprylic acid triglyceride. In some embodiments, the stable anhydrous selenium disulfide formulations described herein further comprise mineral oil.

In some embodiments, the amount of mineral oil in the stable anhydrous selenium disulfide formulations described herein ranges from about 10% to about 97.5%. In some embodiments, the amount of caprylic acid triglyceride in the stable anhydrous selenium disulfide formulations described herein ranges from about 5% to about 50%.

In some embodiments, the amount of vaseline in the stable anhydrous selenium disulfide formulations described herein ranges from about 10% to about 97.5%. In some embodiments, the amount of waxes in the stable anhydrous selenium disulfide formulations described herein ranges from about 5% to about 50%.

In some embodiments, the stable anhydrous selenium disulfide formulations described herein, further comprise a silicone based excipient. In some embodiments, the silicone based excipient is chosen from dimethiconol, dimethicone, cyclopentasiloxane, decamethylcyclopentasiloxane, alkylmethyl siloxane copolyol, alkylmethyl siloxane and stearyltrimethylsilane or any silicone excipient blend suitable for the stable anhydrous selenium disulfide formulations according to the embodiments provided herein. In some embodiments, the silicone based excipient is dimethicone. In some embodiments, the silicone based excipient is stearyltrimethylsilane and stearyl alcohol.

In some embodiments, the stable anhydrous selenium disulfide formulations described herein further comprise a cellulose-derived solidifying agent. In some embodiments the cellulose-derived solidifying agent is microfibrillated cellulose. In some embodiments the cellulose-derived solidifying agent is nanocrystalline cellulose.

In some embodiments, the stable anhydrous selenium disulfide formulations described herein, further comprise a solidifying agent such as fumed silica, hydrogenated vegetable oils or waxes. In some embodiments, the fumed silica is Aerosil® fumed silica.

In some embodiments, the stable anhydrous selenium disulfide formulations described herein, further comprise squalene or squalene.

In some embodiments, the amount of squalene in the stable anhydrous selenium disulfide formulations described herein ranges from about 10% to about 97.5%. In some embodiments, the amount of squalene in the stable anhydrous selenium disulfide formulations described herein ranges from about 5% to about 30%.

Preventing leakage of selenium disulfide from the eye lids to the ocular surface is not desirable since its target organ, the meibomian gland and it orifices can only be reached from the lid edge and thus any spillage of the drug into the fornix' and onto the ocular surface reduces its effectiveness. Furthermore, avoiding leakage of selenium disulfide onto the aqueous ocular surface is desired so it does not aggregate and create large particles that can cause discomfort. In some embodiments the formulation has a specific melting point to allow stable and persistent presence of the ointment over the eyelid with minimal leak onto the ocular surface, yet, enables its penetration to the meibomian orifices, as well as liquefaction of the natural meibum lipids. Described herein in some embodiments is an ointment composition which is semi-solid at room temperature and has melting temperature between 33° C. to 36° C. In some embodiments is provided an ointment composition which is semi-solid at room temperature and has melting temperature between 33° C. to 46° C. In some embodiments is provided an ointment composition which is semi-solid at room temperature and has melting temperature between 33° C. to 38° C. In some embodiments is provided an ointment composition which is semi-solid at room temperature and has melting temperature between 33° C. to 40° C. In some embodiments is provided an ointment composition which is semi-solid at room temperature and has melting temperature between 33° C. to 42° C. In some embodiments is provided an ointment composition which is semi-solid at room temperature and has melting temperature between 33° C. to 44° C. In some embodiments is provided an ointment composition which is semi-solid at room temperature and has melting temperature between 34° C. to 37° C. In some embodiments is provided an ointment composition which is semi-solid at room temperature and has melting temperature between 35° C. to 38° C. In some embodiments is provided an ointment composition which is semi-solid at room temperature and has melting temperature between 32° C. to 40° C. In some embodiments is provided an ointment composition which is semi-solid at room temperature and has melting temperature between 33° C. to 56° C., wherein the composition releases squalene or other liquid lipids upon contact with eyelid margin. In some embodiments the formulation has a melting point that is higher than the temperature of the ocular surface which is about 34° C. so it does not liquefy when it comes in contact with the ocular surface but below 37° C. so it can penetrate the meibomian gland orifices.

Thin Layer of Drug Over Lid Margin

Lipid ophthalmic drug formulations are typically not well tolerated by patients since they get mixed into the tear fluid and cause blurred vision and also stick to the eye lashes and cause unpleasant sensation. It is therefore desired to provide a formulation that will not cause either of these side effects. In one embodiment of the present invention the formulation has viscosity characteristics that cause it to spread over the lid margin at a thickness of between 25 and 200 microns and preferably around 100 microns to allow enough drug to be in contact with the meibomian gland orifices while not creating a surplus of drug that would mix with the tear firm or stick to the eye lashes.

Agglomeration and Ophthalmic Compositions

Major problems related to ophthalmic compositions are crystallization and agglomeration of active ingredients during preparation as well as during storage. Crystallization or agglomeration of active pharmaceutical ingredient (API) leads to non-uniformity of dose, difficulty of administration, irritation to eye due to large drug particles and/or any ocular adverse effect due to high drug concentration or failure of treatment due to low drug concentration. Where the ophthalmic formulations are prepared as suspension, it is desirable to prepare the suspension in a manner such that the suspended particles do not agglomerate into larger ones upon storage. A particle size above 10 µm in diameter in an ophthalmic composition may result in a foreign body sensation in the eye following ocular application, causing reflex tearing. A reduction in particle size generally improves the patient comfort and acceptability of ophthalmic formulations. In addition, reduced particle size will increase the contact area between the selenium disulfide particles and the orifice of the meibomian gland thus increasing the effectiveness of the formulation.

Selenium disulfide forms agglomerates under aqueous conditions. Contacting selenium disulfide with aqueous medium causes immediate and spontaneous aggregation, causing selenium disulfide particles, with an initial average diameter of 5 to 10 µm, to aggregate into large clumps of 50 to 500 µm average diameter.

In some embodiments, the stable anhydrous selenium disulfide formulations described herein are substantially free of agglomerates. In some embodiments, substantially free of agglomerates means that the average selenium disulfide particle diameter throughout the formulation is less than about 50 µm, less than about 45 µm, less than about 40 µm, less than about 35 µm, less than about 30 µm, less than about 25 µm, less than about 20 µm, less than about 15 µm, less than about 10 µm, less than about 9 µm, less than about 8 µm, less than about 7 µm, less than about 6 µm, or less than about 5 µm. In some embodiments, substantially free of agglomerates means that the average selenium disulfide particle diameter throughout the formulation is no more than about 50 µm, no more than about 45 µm, no more than about 40 µm, no more than about 35 µm, no more than about 30 µm, no more than about 25 µm, no more than about 20 µm, no more than about 15 µm, no more than about 10 µm, no more than about 9 µm, no more than about 8 µm, no more than about 7 µm, no more than about 6 µm, or no more than about 5 µm. In some embodiments, substantially free of agglomerates means that the average selenium disulfide particle diameter throughout the formulation is between about 5 µm and about 10 µm, or between about 5 µm and about 15 µm, or between about 10 µm and about 20 µm, or between about 5 µm and about 20 µm, or between about 15 µm and about 25 µm. In some embodiments, substantially free of agglomerates means that the formulation contains less than about 10%, less than about 9%, less than about 8%, less than about 7%, less than about 6%, less than about 5%, less than about 4%, less than about 3%, less than about 2.5%, less than about 2%, less than about 1.5%, less than about 1%, less than about 0.9%, less than about 0.8%, less than about 0.7%, less than about 0.6%, less than about 0.5%, less than about 0.5%, less than about 0.4%, less than about 0.3%, less than about 0.2%, or less than about 0.1% of agglomerates. In some embodiments, substantially free of agglomerates means that the selenium disulfide particle diameter increases no more than 10 times, no more than 9 times, no more than 8 times, no more than 7 times, no more than 6 times, no more than 5 times, no more than 4 times, no more than 3 times, no more than 2 times, or no more than 1.5 times upon formulation compared with the initial particle diameter.

In some embodiments, substantially free of agglomerate means that the formulation does not contains any selenium disulfide agglomerate. In some embodiments, the stable anhydrous selenium disulfide formulations described herein do not contain particles larger than 5 µm in diameter. In some embodiments, the stable anhydrous selenium disulfide formulations described herein do not contain particles larger than 10 µm in diameter. In some embodiments, the stable anhydrous selenium disulfide formulations described herein do not contain particles larger than 20 µm in diameter. In some embodiments, the stable anhydrous selenium disulfide formulations described herein do not contain particles larger than 10 µm in diameter and do not contain any surfactants and dispersing agents. In some embodiments, the stable anhydrous selenium disulfide formulations described herein is substantially free of surfactants and dispersing agents. In some embodiments, substantially free of surfactants and dispersing agents means that the formulation contains less than about 10% surfactants, dispersing agents, and combination thereof. In some embodiments, substantially free of surfactants and dispersing agents means that the formulation contains less than about 10%, less than about 9%, less than about 8%, less than about 7%, less than about 6%, less than about 5%, less than about 4%, less than about 3%, less than about 2.5%, less than about 2%, less than about 1.5%, less than about 1%, less than about 0.9%, less than about 0.8%, less than about 0.7%, less than about 0.6%, less than about 0.5%, less than about 0.5%, less than about 0.4%, less than about 0.3%, less than about 0.2%, or less than about 0.1% surfactants, dispersing agents, and combination thereof. In some embodiments, substantially free of surfactants and dispersing agents means that the formulation contains no more than about 10% surfactants, dispersing agents, and combination thereof. In some embodiments, substantially free of surfactants and dispersing agents means that the formulation contains no more than about 10%, no more than about 9%, no more than about 8%, no more than about 7%, no more than about 6%, no more than about 5%, no more than about 4%, no more than about 3%, no more than about 2.5%, no more than about 2%, no more than about 1.5%, no more than about 1%, no more than about 0.9%, no more than about 0.8%, no more than about 0.7%, no more than about 0.6%, no more than about 0.5%, no more than about 0.5%, no more than about 0.4%, no more than about 0.3%, no more than about 0.2%, or no more than about 0.1% surfactants, dispersing agents, and combination thereof. In some embodiments, substantially free of surfactants and dispersing agents means that the formulation does not contains any surfactants, dispersing agents, and combination thereof. In some embodiments, substantially free of surfactants and dispersing agents means that the formulation is free of surfactants, dispersing agents, and combination thereof.

In some embodiments, the stable anhydrous selenium disulfide formulations described herein comprise a dispersion of selenium disulfide in an anhydrous semi-solid base. In some embodiments, the selenium sulfide is dispersed in the anhydrous base to form a homogenous dispersion without any large aggregates or clumps of particles. In some embodiments, the topical administration of a homogenous dispersion of selenium disulfide in an anhydrous semi-solid base, as described herein, to the eyelid margin of a patient, for treating meibomian gland dysfunction, does not cause any irritation to the eyes of the patient.

Chemical and Storage Stability of Selenium Disulfide Dispersion in Anhydrous Semi-Solid Ophthalmic Base Prior to the disclosures provided herein, surfactants and various suspending agents were required to stabilize selenium disulfide suspension in liquid and semi-solid dosage forms, and enable its topical application. The stable anhydrous selenium disulfide formulations described herein, in some embodiments, unexpectedly are stable without the use of surfactants or suspending agents or dispersing agents.

In some embodiments, the stable anhydrous selenium disulfide formulations described herein are physically stabilized against aggregation and chemically stabilized against degradation without the addition of surfactants, dispersing agents, or suspending agents.

In some embodiments, the stability of the formulations is tested under accelerated stability conditions, at a temperature between about of 40° C. and 60° C. for an extended storage period.

Stability of an ophthalmic formulation is determined by the extent of chemical degradation of the active ingredients via processes such as hydrolysis, oxidation, etc, during the period of storage.

Chemical Degradation is Characterized by Formation of Degradants

In some embodiments, the total amount of degradants in the stable anhydrous selenium disulfide formulations described herein does not increase over time during storage period. In some embodiments, the total amount of degradants in the stable anhydrous formulations described herein does not increase when the formulation is tested under accelerated stability conditions, at a temperature of about 40° C. and 60° C. and the degradation observed is lower in comparison to marketed $SeS_2$ drug products. Another embodiment provides the composition further comprising small amounts of degradants of selenium disulfide, and wherein the amount of the degradants does not increase above 1% of the total weight of the composition.

In some embodiments, the chemical stabilization of the stable anhydrous selenium disulfide formulations described herein is attributed to the reduced water content of the formulations. In some embodiments, the chemical stabilization of the stable anhydrous selenium disulfide formulations described herein is attributed to the anhydrous nature of the formulation. In some embodiments, the chemical stabilization of the stable anhydrous selenium disulfide formulations described herein is attributed to the lack of polyoxyethylene comprising stabilizing emulsifiers and dispersing agents in the formulation In some embodiments, drug instability in pharmaceutical formulations is detected by a change in the physical appearance, color, odor, taste, or texture of the formulation. In some embodiments, the stable anhydrous selenium disulfide formulations described herein do not exhibit any substantial change in color during a period of storage, under elevated temperatures. In some embodiments, the period of storage is two weeks at a temperature of about 60° C.

Melting Point of Stable Anhydrous Selenium Disulfide Formulations

In some embodiments, the stable anhydrous selenium disulfide formulations described herein has a melting temperature between about 34° C. and about 50° C. In some embodiments, the stable anhydrous selenium disulfide formulations described herein has a melting temperature of about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments, the stable anhydrous selenium disulfide formulations described herein has a melting temperature close to and above the temperature of eyelid margin. In some embodiments, the melting point of the stable anhydrous selenium disulfide formulations described herein increases the bioavailability and efficacy of selenium disulfide.

Solid and Semi-Solid Dosage Form Composition Comprising Selenium Disulfide Dispersion in Anhydrous Semi-Solid Ophthalmic Base In some embodiments, the stable anhydrous selenium disulfide formulations described herein are part of a solid dosage form like a lip balm or a stick product, that is convenient to apply and spread over the eye lid margin in a similar manner to cosmetic eye lid product, whereas a very small amount of drug product is applied directly and precisely on the eye lid margin.

In some embodiments, the amount of drug product applied to the eye lid margin is about one mg. In other embodiments, the amount of drug product applied to the eye lid margin is less than 5 mg, less than 4 mg, less than 3 mg, or less than 2 mg.

In some embodiment, the stable anhydrous selenium disulfide composition comprises a synthetic or natural antioxidant selected from, for example, tocopherol or Vitamin E, EDTA (ethylenediamine tetraacetate), butylated hydroxyl anisole, butylated hydroxyl toluene, glutathione, astaxanthin, lutein, lycopene, propyl gallate, rosmarinic acid or ascorbyl palmitate.

In some embodiments, the stable anhydrous selenium disulfide formulations described herein are part of a semi-solid dosage form, such as an eye liner or a ointment product, that is convenient to apply and spread over the eye lid margin in a similar manner to cosmetic eye lid product, whereas a very small amount of drug product is applied directly and precisely on the eye lid margin.

Meibomian Gland

The meibomian glands are large sebaceous glands located in the eyelids, and unlike skin, are unassociated with hair. The meibomian glands produce the lipid layer of the tear film that protects it against evaporation of the aqueous phase. The meibomian gland orifice is located on the epithelial side of the lid margin, and is only a few hundred microns from the mucosal side. The glands are located on both upper and lower eyelids, with higher amounts of the glands on the upper eyelid. A single meibomian gland is composed of clusters of secretory acini that are arranged circularly around a long central duct and connected to it by short ductules. The terminal part of the central duct is lined by an ingrowth of the epidermis that covers the free lid margin and forms a short excretory duct that opens as an orifice at the posterior part of the lid margin just anterior to the mucocutaneous junction near the inner lid border. The oily secretion composed of lipids is synthesized within the secretory acini. The lipid secretion is a liquid at near body temperature and is delivered to the skin of the lid margin as a clear fluid, called "meibum." It forms shallow reservoirs on the upper and lower lid margins, and consists of a complex mixture of cholesterol, wax, cholesteryl esters, phospholipids, with small amounts of triglycerides, triacylglycerols, and hydrocarbons. The separate meibomian glands are arranged in parallel, and in a single row throughout the length of the tarsal plates in the upper and lower lids. The extent of the glands corresponds roughly to the dimensions of the tarsal plates.

Meibomian Gland Dysfunction (MGD)

The term, "meibomian gland dysfunction," as used herein, refers to chronic, diffuse abnormality of the meibomian glands that is characterized by terminal duct obstruction, or qualitative or quantitative changes in the glandular secretion, or both. MGD may result in alteration of the tear film viscosity, eye irritation symptoms, inflammation, or ocular surface disease. The most prominent aspects of MGD are obstruction of the meibomian gland orifices and terminal ducts and changes in the meibomian gland secretions.

MGD is a leading contributor of dry eye syndrome. The occurrence of dry eye syndrome is widespread and affects about 20 million patients in the United States alone. Dry eye syndrome is a disorder of the ocular surface resulting from either inadequate tear production or excessive evaporation of moisture from the surface of the eye. Tears are important to corneal health because the cornea does not contain blood vessels, and relies on tears to supply oxygen and nutrients. Tears and the tear film are composed of lipids, water, and mucus, and disruption of any of these can cause dry eye. MGD is not synonymous with posterior blepharitis, which describes inflammatory conditions of the posterior lid margin. MGD may cause posterior blepharitis, but MGD may not always be associated with inflammation or posterior blepharitis. MGD also refers to functional abnormalities of the meibomian gland, while "meibomian gland disease," describes a broad range of meibomian gland disorders, that includes neoplasia and congenital disease. Clinical signs of MGD include meibomian gland dropout, altered meibomian gland secretion, and changes in lid morphology.

Pharmaceutical Excipient

In other embodiments, the topical compositions described herein are combined with a pharmaceutically suitable or acceptable carrier (e.g., a pharmaceutically suitable (or acceptable) excipient, physiologically suitable (or acceptable) excipient, or physiologically suitable (or acceptable) carrier). Exemplary excipients are described, for example, in *Remington: The Science and Practice of Pharmacy* (Gennaro, 21$^{st}$ Ed. Mack Pub. Co., Easton, Pa. (2005)).

Methods of Treatment utilizing stable anhydrous selenium disulfide formulations

Described herein are methods for treating meibomian gland dysfunction in a patient in need comprising topical administration of a stable anhydrous selenium disulfide formulation to the eyelid margin of the patient in need. There are two potential categories of administration. One occurs with the assistance of a health-care provider: this category includes both acute and maintenance uses of the stable anhydrous selenium disulfide formulation. An acute use, in one embodiment, requires a stronger stable anhydrous selenium disulfide formulation (either in terms of concentration of the selenium disulfide or the inherent activity of the selenium disulfide). A maintenance use, in one embodiment, allows for the use of lower concentrations of the selenium disulfide, or selenium disulfide with lower inherent activity. A maintenance use, in one embodiment, involves a patient at a routine visit to the health care provider. Both acute uses and maintenance uses optionally involve use of an eye-protecting device or apparatus. In one embodiment, the acute use is performed by the health care provider, and the maintenance use is performed by the patient or non-health care provider. The second potential category of administration does not occur with the active assistance of a health care provider, but rather involves the patient applying the stable anhydrous selenium disulfide formulation to his/her eyelid margin. In one embodiment, such administration occurs over an extended period of time; one way of describing this patient-administered multi-administration mode is as a chronic use. In general, different or second formulations of the stable anhydrous selenium disulfide formulation are recommended for chronic or patient-administered uses. In one embodiment the different or second formulation utilizes a lower concentration of the stable anhydrous selenium disulfide formulation. In another embodiment, the second or different formulation utilizes a stable anhydrous selenium disulfide formulation that has a lower activity than the first formulation.

Provided herein is a method for treating meibomian gland dysfunction in a patient in need thereof, comprising topically administering to the patient a composition that reaches the eyelid margin of the patient, wherein the composition comprises a therapeutically-effective amount of stable anhydrous selenium disulfide formulation. One embodiment provides the method wherein the concentration of the stable anhydrous selenium disulfide in the composition is between about 0.1% to about 10%. One embodiment provides the method wherein composition is topically administered to the patient until the keratinized obstruction is relieved. One embodiment provides the method wherein composition is topically administered to the patient periodically after relieving the keratinized obstruction. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

Provided herein is a method for treating meibomian gland dysfunction in a patient in need thereof, comprising topically administering to the patient a composition that reaches the eyelid margin of the patient, wherein the composition consists essentially of a therapeutically-effective amount of stable anhydrous selenium disulfide formulation. One embodiment provides the method wherein the concentration of the stable anhydrous selenium disulfide in the composition is between about 0.1% to about 10%. One embodiment provides the method wherein composition is topically administered to the patient until the keratinized obstruction is relieved. One embodiment provides the method wherein composition is topically administered to the patient periodically after relieving the keratinized obstruction. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

It should be understood that the present methods also include the physical removal of the obstruction in the meibomian gland, followed by chronic and/or maintenance administration of the stable anhydrous selenium disulfide formulations described herein.

Provided herein is a method for removing a keratin obstruction from a meibomian gland in a patient in need thereof, comprising topically administering to the patient a composition that reaches the eyelid margin of the patient, wherein the composition comprises a therapeutically-effective amount of stable anhydrous selenium disulfide formulation. One embodiment provides the method wherein the concentration of the stable anhydrous selenium disulfide in the composition is between about 0.1% to about 10%. One embodiment provides the method wherein composition is topically administered to the patient until the keratinized obstruction is relieved. One embodiment provides the method wherein composition is topically administered to the patient periodically after relieving the keratinized obstruction. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

Provided herein is a method for removing a keratin obstruction from a meibomian gland in a patient in need thereof, comprising topically administering to the patient a composition that reaches the eyelid margin of the patient, wherein the composition consists essentially of a therapeutically-effective amount of stable anhydrous selenium disulfide formulation. One embodiment provides the method wherein the concentration of the stable anhydrous selenium disulfide in the composition is between about 0.1% to about 10%. One embodiment provides the method wherein composition is topically administered to the patient until the keratinized obstruction is relieved. One embodiment provides the method wherein composition is topically administered to the patient periodically after relieving the keratinized obstruction. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

In some embodiments, topical administration of the composition comprising a selenium disulfide pharmacological agent and an anhydrous semi-solid ophthalmic base occurs twice a week. In some embodiments, topical administration of the composition comprising a selenium disulfide pharmacological agent and an anhydrous semi-solid ophthalmic base occurs every other day. In some embodiments, topical administration of the composition comprising a selenium disulfide pharmacological agent and an anhydrous semi-solid ophthalmic base occurs every day. In some embodiments, topical administration of the composition comprising a selenium disulfide pharmacological agent and an anhydrous semi-solid ophthalmic base occurs several times a day.

In some embodiments, the composition for topical administration is a liquid or a semi-solid. In some embodiments, the composition for topical administration is an emulsion semi-solid. In some embodiments, the composition for topical administration is a cream. In some embodiments, the composition for topical administration is an ointment. In some embodiments, meibomian gland opening pharmacological agent is suspended within the composition. In some embodiments, the composition for topical administration is a lotion. In some embodiments, the composition for topical administration is a gel. In some embodiments, the composition for topical administration is an anhydrous dispersion. In some embodiments, the composition for topical administration is an anhydrous lip balm or stick formulation or a device that enable the patient to target the eye lid margin.

One embodiment provides a method for treating a hyperkeratosis disorder in a patient in need thereof comprising topically administering to the eyelid margin of the patient a composition comprising a therapeutically-effective amount of a stable anhydrous selenium disulfide formulation, wherein the hyperkeratosis disorder is selected from meibomian gland dysfunction, or dry eye. Another embodiment provides the method wherein the hyperkeratosis disorder is meibomian gland dysfunction. Another embodiment provides the method wherein the hyperkeratosis disorder is dry eye.

One embodiment provides a method for removing a keratin obstruction of the meibomian gland in a patient having a hyperkeratosis disorder comprising topically administering to the eyelid margin of the patient a composition comprising a therapeutically-effective amount of a stable anhydrous selenium disulfide formulation, wherein the hyperkeratosis disorder is selected from meibomian gland dysfunction, or dry eye. Another embodiment provides the method wherein the hyperkeratosis disorder is meibomian gland dysfunction. Another embodiment provides the method wherein the hyperkeratosis disorder is dry eye.

One embodiment provides a method for treating an ophthalmic disorder caused by keratin obstruction of the meibomian gland in a patient in need thereof comprising topically administering to the eyelid margin of the patient a composition comprising a therapeutically-effective amount of a stable anhydrous selenium disulfide formulation, wherein the ophthalmic disorder is meibomian gland dysfunction or dry eye. Another embodiment provides the method wherein the ophthalmic disorder is meibomian gland dysfunction. Another embodiment provides the method wherein the ophthalmic disorder is dry eye.

Certain Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 10% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The terms "treat," "treating," or "treatment" as used herein, include reducing, alleviating, abating, ameliorating, relieving, or lessening the symptoms associated with MGD in either a chronic or acute therapeutic scenario. In one embodiment, treatment includes a reduction of a terminal duct obstruction.

The term "recurrence," or "reducing relapse" refers to return of MGD symptoms in a chronic therapeutic scenario.

The term "opening" refers to the clearing (at least in part) of an obstructed meibomian gland canal or orifice and/or maintaining the patency of the meibomian gland canal or orifice.

The term "anhydrous" as used herein refers to a composition containing less than 2% water by weight, or less than 1% water by weight, or a composition which does not contain any water.

The term "dispersion" as used herein refers to a system in which particles are dispersed in a continuous phase of a different composition or state. The dispersions are solid dispersions.

The term "agglomerates", "aggregates", and "clumps of particles" as used herein refers to a collection of particles. The terms are intended to be synonymous to each other and are used interchangeably.

The term "color stability" as used herein refers to the ability of a composition to substantially retain its original color during the time of storage. The term "substantially retain" means that there are no visually discernable changes in the color of the formulation over the time of storage or use.

The term "lotion" describes an emulsion liquid dosage form. This dosage form is generally for external application to the skin (US FDA Drug Nomenclature Monograph, number C-DRG-00201).

The term "cream" describes an emulsion semisolid dosage form, usually containing >20% water and volatiles and/or <50% hydrocarbons, waxes or polyols as the vehicle. A cream is more viscous than a lotion. This dosage form is generally for external application to the skin (US FDA Drug Nomenclature Monograph, number C-DRG-00201).

The term "ointment" describes a semisolid dosage form, usually containing <20% water and volatiles and/or >50% hydrocarbons, waxes or polyols as the vehicle. This dosage form is generally for external application to the skin or mucous membranes (US FDA Drug Nomenclature Monograph, number C-DRG-00201).

The term "solution" describes a clear, homogeneous liquid dosage form that contains one or more chemical substances dissolved in a solvent or mixture of mutually miscible solvents (US FDA Drug Nomenclature Monograph, number C-DRG-00201).

The term "suspension" refers to a heterogeneous mixture containing solid particles that are sufficiently large for sedimentation.

EXAMPLES

Example 1: Stable Anhydrous Selenium Disulfide Formulations

Several formulations of anhydrous selenium disulfide were prepared and the detailed compositions are listed in Table 1.

TABLE 1

Exemplary formulations of anhydrous selenium disulfide

| Ingredients | FO2 % W/W | FS2 % W/W | FA1 % W/W | FM1 % W/W | FM2 % W/W | FM3 % W/W |
|---|---|---|---|---|---|---|
| Selenium disulfide | 2.5 | 2.5 | 2.5 | 2.5 | 2.5 | 2.5 |
| Mineral oil | 20 | — | 72.5 | 97.5 | — | 30 |
| Vaseline | 62.5 | 32.5 | — | — | 97.5 | 67.5 |
| Capric caprylic triglyceride | 10 | 10 | 20 | — | — | — |
| Dimethicone (Dow corning) | — | 40 | — | — | — | — |
| Wax 10 (Dow corning) | — | 10 | — | — | — | — |
| Squalane | 5 | 5 | — | — | — | — |
| Fumed silica Aerosil 200 | — | — | 5 | — | — | — |

Example 2: Dispersion of SeS$_2$ in Aqueous and Anhydrous Medium

Figure 2A:
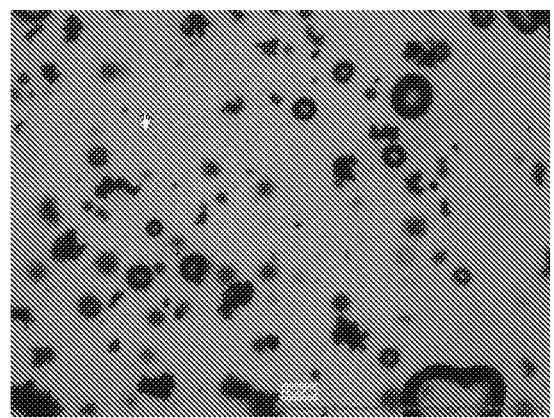
FIGS. 2A and 2B correspond to microscopic image of anhydrous selenium disulfide formulation FO2 and FS2 respectively, at 100× magnification.
Figure 2B:
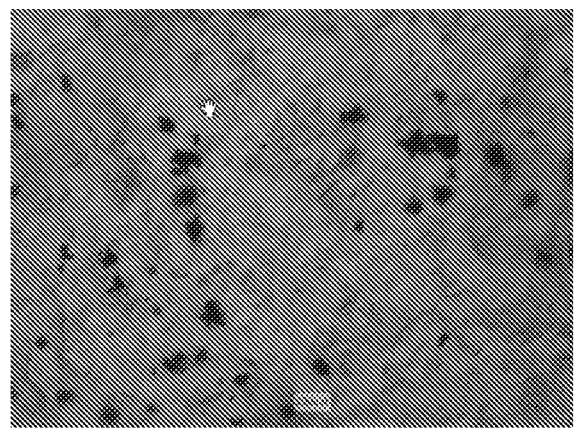

Microscopic images were acquired of Selenium disulfide dispersions in either aqueous mediums or anhydrous ointments, and Sebosel™ (containing 2.5% selenium disulfide). The aqueous dispersions of 2.5% selenium disulfide in water or Carbopol™ gel were found to form clumps or aggregates or agglomerates, as shown in FIGS. 1 A-C. In contrast, the selenium sulfide formulations FO2 and FS2, containing 2.5% selenium disulfide dispersed in anhydrous ointments were found to be smooth homogenous dispersions and did not contain any large clumps or aggregates or agglomerates, as shown in FIGS. 2 A-B.

Example 3: Anhydrous Selenium Disulfide Stability Study by Change of Color

Stability of an exemplary anhydrous selenium disulfide formulation, FO2, was tested by monitoring whether the formulation changed color during a storage period of two weeks at 60° C. As shown in Table 2, the FO2 formulation did not change color under the test conditions, whereas Sebosel™, which contains 2.5% selenium disulfide dispersed in an aqueous medium, changed color from orange to deep brown. The results indicate that the anhydrous selenium disulfide formulations described herein, have improved physical stability and improved shelf-life.

TABLE 2

Comparison of stability of anhydrous selenium disulfide and Sebosel™

| Formulation | Color | 2 weeks 60° C. |
|---|---|---|
| Sebosel ™ | Orange | Deep brown |
| FO2 | Orange | Orange |

TABLE 3

Examples of semi solid and solid type anhydrous formulations of SeS$_2$

| | LBM29 % W/W | LBM35 % W/W | LBM36 % W/W | LBM37 % W/W | LBM38 % W/W |
|---|---|---|---|---|---|
| SeS$_2$ | 1 | 1 | 1 | 1 | 1 |
| Microcrystalline wax | | | | 10 | |
| Vaseline | 7 | 7 | 7 | 7 | 7 |
| Lanolin | 6 | 6 | 6 | 6 | 6 |
| Capric/caprylic triglycerides | 39 | 35.5 | 33 | 28 | 28 |
| Squalane | 39 | 35.5 | 33 | 28 | 28 |
| Hydrogenated Vegetable Oil | 8 | 15 | 20 | 20 | 30 |
| Total | 100 | 100 | 100 | 100 | 100 |

The formulations of Table 3, were placed in 40° C. and 60° C. stability chamber and show less change of color in comparison to marketed SeS$_2$ drug products, and with various melting point and spread ability and viscosity or hardness.

TABLE 4 examples of semi solid and solid type anhydrous formulations of SeS$_2$

| | LBM53 % W/W | LBM59 % W/W | LBM60 % W/W | LBM61 % W/W | LBM63 % W/W | LBM64 % W/W | LBM65 % W/W | LBM66 % W/W |
|---|---|---|---|---|---|---|---|---|
| SeS2 | 0.5 | 0.5 | 0.5 | 0.5 | 0.5 | 0.5 | 0.5 | 0.5 |
| Microcristalline wax | 25 | 33 | 25 | 25 | 25 | | | |
| Vaseline | 20.5 | 10.5 | 20.5 | 20.5 | 24 | 24 | 24 | 24 |
| Capric/caprylic acid (TCC) | 17 | 17 | 34 | 17 | 17 | 17 | 17 | 17 |
| Squalane | 17 | 17 | | 12 | 7.9 | 7.9 | 7.9 | 7.9 |
| Mineral oil | | | | | | 25 | 30 | 40 |
| Cutina HR PH (Hydrogenated castor oil) | 20 | 20 | 10 | 20 | 20 | 20 | 20 | 10 |

TABLE 4-continued examples of semi solid and solid type anhydrous formulations of SeS$_2$

|  | LBM53 % W/W | LBM59 % W/W | LBM60 % W/W | LBM61 % W/W | LBM63 % W/W | LBM64 % W/W | LBM65 % W/W | LBM66 % W/W |
|---|---|---|---|---|---|---|---|---|
| Dermofeel viscolid |  |  | 10 |  | 5 | 5 |  |  |
| Dimethicone (Dow C.) |  | 2 |  |  |  |  |  |  |
| TPGS |  |  |  | 5 |  |  |  |  |
| Tocopherol |  |  |  |  | 0.5 | 0.5 | 0.5 | 0.5 |
| BHT |  |  |  |  | 0.1 | 0.1 | 0.1 | 0.1 |
| Total | 100 | 100 | 100 | 100 | 100 | 100 | 100 | 100 |
| Consistency 1 to 5 | 4 | 4 | 5 | 5 | 5 | 1 | 1 | 1 |
| Spreadability 1 to 5 | 4 | 3 | 5 | 5 | 5 | 1 | 1 | 1 |
| 60 C. few days | 5 | 5 | 3 | 3 | 5 | 5 | 5 | 5 |

*Score 1 to 5: 5 is the highest or best results and 1 is worst or low result

Formulations 53, 59, 60, 61 and 63 are hard and formulations 64, 65 and 66 are soft type. The hard formulations show better spread ability formulations 60 and 61 show some change of color at accelerated stability test at 60° C. whereas all other formulations did not changed color over a few days at 60° C. whereas Sebosel™ lost its typical orange color and became dark brown. Moreover, formulations 64, 65 and 66 did not change color over at least three weeks at 60° C. All formulations exhibited very fine and uniform dispersion of SeS$_2$ and no aggregation at regular and accelerated stability conditions. Formulations 53, 59, 60, 61 and 63 did not change color over at least one month at 40° C. Formulations 64, 65 and 66 did not change color over at least three months at 40° C.

Example 4: Destabilizing Inactive Ingredients

Formulations that contained inactive ingredients comprising polyethylene glycol moiety, such as tween or pluronic or tocopherol polyethyelene glycol or vinylpyrrolidone comprising molecules, reduced SeS$_2$ chemical stability and a black color was observed within two hours to two days upon storage at 60° C.

What is claimed is:

1. A composition comprising selenium disulfide and an anhydrous semi-solid ophthalmic base, wherein the composition is substantially free of selenium disulfide agglomerates, wherein the composition is substantially free of surfactants and dispersing agents, and wherein the composition is suitable for topical administration on the eyelid margin.

2. The composition of claim 1, wherein the selenium disulfide is dispersed in the anhydrous semi-solid ophthalmic base.

3. The composition of claim 1, wherein the anhydrous semi-solid ophthalmic base is an oleaginous base selected from the group consisting of petroleum, white petroleum, mineral oil, vegetable oils and combinations thereof.

4. The composition of claim 1, wherein the composition or base thereof has a melting point between about 34° C. and about 50° C.

5. The composition of claim 1, wherein the composition further comprises squalene or hydrogenated oil.

6. The composition of claim 1, wherein any selenium disulfide agglomerates within the composition have a particle diameter of less than about 50 μm.

7. The composition of claim 1, wherein the composition has an average selenium disulfide particle diameter of between about 5 μm and about 10 μm.

8. The composition of claim 1, wherein the composition is chemically and/or physically stable.

9. The composition of claim 1, wherein the composition does not contain particles, including agglomerates, larger than 20 μm in diameter.

10. The composition of claim 1, wherein the composition does not contain particles, including agglomerates, larger than 5 μm in diameter.

11. A method for treating meibomian gland dysfunction in a patient in need thereof, comprising topically administering to the eyelid margin of the patient a composition comprising selenium disulfide and an anhydrous semi-solid ophthalmic base, wherein the composition is substantially free of selenium disulfide agglomerates, and wherein the composition is substantially free of surfactants and dispersing agents.

12. The method of claim 11, wherein the selenium disulfide is dispersed in the anhydrous semi-solid ophthalmic base having a melting point of about 34° C. to about 50° C.

13. The method of claim 11, wherein the anhydrous semi-solid ophthalmic base is an oleaginous base selected from the group consisting of petroleum, white petroleum, mineral oil, vegetable shortenings and combinations thereof.

14. The method of claim 11, wherein the composition for topical administration further comprises squalene or hydrogenated oil.

15. The method of claim 11, wherein the meibomian gland dysfunction is characterized by obstruction of meibomian gland.

16. The method of claim 11, wherein any selenium disulfide agglomerates within the composition have an average selenium disulfide particle diameter of less than about 50 μm.

17. The method of claim 11, wherein the composition has an average selenium disulfide particle diameter of between about 5 μm and about 10 μm.

18. The method of claim 11, wherein the composition does not contain particles, including agglomerates, larger than 20 μm in diameter.

19. The method of claim 11, wherein the composition does not contain particles, including agglomerates, larger than 5 μm in diameter.

20. A composition comprising selenium disulfide particles and a semi-solid ophthalmic base, wherein the selenium disulfide particles have an average diameter of less than 20 μm.

21. The composition of claim 20, wherein the composition is substantially free of surfactants and dispersing agents.

22. The composition of claim 20, wherein the composition does not contain selenium disulfide particles larger than 20 μm in diameter.

\* \* \* \* \*